(12) United States Patent
Zunino, III et al.

(10) Patent No.: US 8,722,418 B1
(45) Date of Patent: May 13, 2014

(54) THERMAL INDICATING COMPOSITION

(75) Inventors: James L. Zunino, III, Boonton Township, NJ (US); Zafar Iqbal, Morristown, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 90 days.

(21) Appl. No.: 13/413,164

(22) Filed: Mar. 6, 2012

Related U.S. Application Data

(60) Provisional application No. 61/449,816, filed on Mar. 7, 2011.

(51) Int. Cl.
*G01N 31/22* (2006.01)

(52) U.S. Cl.
USPC ........................................ 436/166; 252/408.1

(58) Field of Classification Search
USPC ........................................ 436/166; 252/408.1
See application file for complete search history.

(56) References Cited

PUBLICATIONS

Zunino, III et al., "Thermal indicating paints for ammunition health monitoring", Proc. SPIE 7646, Nanosensors, Biosensors, and Info-Tech Sensors and Systems 2010, 76461K (Mar. 30, 2010); doi:10.1117/12.847654; http://dx.doi.org/10.1117/12.847654.*

* cited by examiner

*Primary Examiner* — Monique Cole
(74) *Attorney, Agent, or Firm* — Henry S. Goldfine

(57) ABSTRACT

A reversible, colored thermal indicating composition, whose chromaticity provides a measure of the elapsed time within specific elevated temperature bands—the composition containing one or more polydiacetylenes (PDAs) in combination with ZnO alloyed with a transition metal oxide, such as $ZrO_2$ and/or $TiO_2$.

10 Claims, 3 Drawing Sheets

THERMAL INDICATING COMPOSITION

CROSS-REFERENCE TO RELATED APPLICATIONS

This application claims the benefit under 35 USC §119(e) of U.S. provisional patent application 61/449,816, filed on Mar. 7, 2011, which provisional application is hereby incorporated by reference.

STATEMENT OF GOVERNMENT INTEREST

The invention described herein may be manufactured, used, imported, sold, and/or licensed by or for the Government of the United States of America for U.S. Government purposes, without the payment or any royalty thereon or therefore.

BACKGROUND OF THE INVENTION

1. Field of the Invention

The present invention relates to thermal indicating compositions, and more specifically to such compositions containing one or more polydiacetylenes (PDAs), plus an oxide, such as ZnO, alloyed with a transition metal oxide, such as $ZrO_2$ and/or $TiO_2$; wherein, such composition will respond repeatedly to thermal stimuli at a desired "trigger" temperature, or wherein, such compositions can be used to establish the cumulative time of exposure to a given thermal stimuli level based upon the resulting chromaticity thereof.

2. Description of the Related Art

Materials that change color in response to external stimuli are known as "chromic materials". Such chromic materials may radiate, lose color, or change properties induced by external stimuli. Different stimuli result in different responses in the material being affected. "Chromic" is a suffix that means color, so chromic materials are named based on the stimuli energy affecting them, for example: (1) photochromic—light, or (2) thermochromic—heat, or (3) piezorochromic—pressure, or (4) solvatechromic—liquid, or (5) electrochromic—electricity/voltage conflicts.

An example of a commercial utilization of thermochromic paint was the paint introduced by Mattel® Toy Corp. in the 1980's applied to their Hot Wheels Color Racers® and Color FX™ cars. These cars were painted with temperature sensitive paint which changed colors when placed in icy cold or warm tap water. These convention types of chromic paints change color upon exposure to certain temperatures, then change back to their initial state (and exhibit their original color) once the stimuli (i.e., temperature) is removed (in this example, the temperature of the paint returns to room temperature), i.e. reversibly.

Polydiacetylenes ("PDAs") are a series of conjugated polymers which can undergo thermochromic transitions when exposed to temperature stimuli. This chromic change, as illustrated in FIG. 1, is caused by decrease of the conjugation length of the polymeric backbone due to strain induced by breaking of hydrogen bonds on the side groups. Therefore, the thermochromic transition temperature is a function of the side groups on the polymeric backbone structures. By changing the side groups, repeatable response to set stimuli are possible, allowing these materials to function as sensors. There are several applications of such PDAs, particularly in the form of coatings or films, as chromic sensors for temperature, chemical, and stress. These polymers are tailored to create inks, paints, and coatings that will, for example, with an irreversible color change indicate that an object has been exposed to a high temperature so as to impact its functionality.

The monomers making up the PDAs are typically colorless and become increasingly colored with polymerization. Color in PDAs occurs as a result of $\pi$ to $\pi^*$ electronic transitions associated with the C≡C—C≡C diacetylene backbone. Reversible changes in the color of the polymer occur due to molecular conformational changes resulting from modifications of the side chain packing, ordering and orientation. This also means that these PDAs will undergo phase changes in two stable states, the low temperature blue state and the high temperature red state. Complete thermochromic reversibility from the red to the blue phase is known to take place in PDAs where sufficiently strong hydrogen bonding interactions exist and are recovered on cooling from the high temperature red state. Recovery of the hydrogen bonding interactions can also be induced by the addition of specific organic molecules. It was therefore surprising that the addition of the inorganic compound ZnO to the PDAs induced chromatic reversibility and a large upshift of the chromatic transition temperature. By contrast, it has been published that the addition of $TiO_2$ and $ZrO_2$ did not affect the chromatic transition parameters.

Cost effective, commercially available, PDA monomers provide irreversible blue to red transitions at temperatures ranging from about 145 to about 172 degrees F.—some examples being:

10,12 pentacosadiynoic acid (PCDA) at about 145° F.,
10,12 tricosadiynoic acid (TCDA) at about 165° F., and
10,12 docosadiynedioic acid (Bis-1) at about 172° F.

However, there are applications where it is necessary to significantly increase these temperature ranges. An important example is what occurred during Desert Storm, where the U.S. forces faced operational temperatures inside munitions' containers exceeded 190° F., i.e. far in excess of the design limits of about 145 to about 165° F. for such munitions.

It is further critical to understand how long a particular munition has been subjected to elevated temperatures over the design limitation thereof—as there are thermal stabilizer(s) provided in military munitions which are depleted over time by such exposure—and as, when such stabilizer(s) is depleted the munition can go critical. Current U.S. Army requirements would have such a means identify/remember/indicate when over any 3 days, an aggregate of 2 hours exposure above 160° F. has occurred. Currently there is no simple, economical means to know that such a period what temperature exposure has occurred with respect to fielded munitions.

Finally, as munitions are stored for extended periods, often greater than 20 years, as well as, being subjected to prolonged and repeated periods of transportation, the use of powered devices and electronics is impractical for temperature monitoring. Further, as stated above, current PDAs are limited with respect to indicating high trigger temperatures and are not known to be capable of identifying a period of exposure to any given temperature level. Therefore, having a non-powered, cost effective, reliable, and easily readable means to measure and indicate exposure to higher temperature levels and to the duration thereof, of a munition is critical to understand if that munition has been compromised and may represent a deadly hazard.

SUMMARY OF THE INVENTION

The present invention addresses the above stated need by providing a PDA based thermochromic compositions that will trigger at higher temperatures than conventional PDA formulations and that will provide a chromaticity (i.e. vividness or dullness of color) indication, at desired thermal bands.

The present invention selectively uses one or a combination of PDAs therein which provide thermochromatic indications of temperature bands above the normal thermochromatic temperature of the PDAs themselves, and which thermochromic compositions can be easily incorporated into paints, inks, and other coatings using known technology. Depending upon the cumulative time of exposure of the subject inventive thermochromic compositions to particular temperature band—the resulting chromaticity of the inventive indicator formulation is indicative of the elapsed time of exposure to the particular thermal band. This resulting chromaticity of a thermal coating incorporating the inventive thermochromic composition is measurable and provides an empirical means to determine the cumulative thermal dwell, or soak time, at the particular temperature band. The subject PDA based thermochromic compositions including:

(a) one or more polydiacetylenes; and
(b) an oxide, ZnO, alloyed with one or more, transition metal oxides, such as $ZrO_2$ and/or $TiO_2$; wherein,
(c) the ZnO and transition metal oxides used are micro scale or smaller particles.

In a preferred embodiment, the one or more polydiacetylenes are one or more of 10,12 pentacosadiynoic acid or "PCDA"), (10,12 tricosadiynoic acid or "TCDA"), and (10,12-docosadiynedioic acid or "Bis-1").

Additional aspects of the invention will be set forth in part in the description which follows, and in part will be obvious from the description. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated herein and constitute part of the specification, illustrate an embodiment of the invention and together with the description, serve to explain the principles of the present invention. The embodiments illustrated herein are presently preferred, it being understood, however, that the invention is not limited to the precise arrangements and instrumentalities shown, wherein.

DETAILED DESCRIPTION OF THE INVENTION

Figure 1:
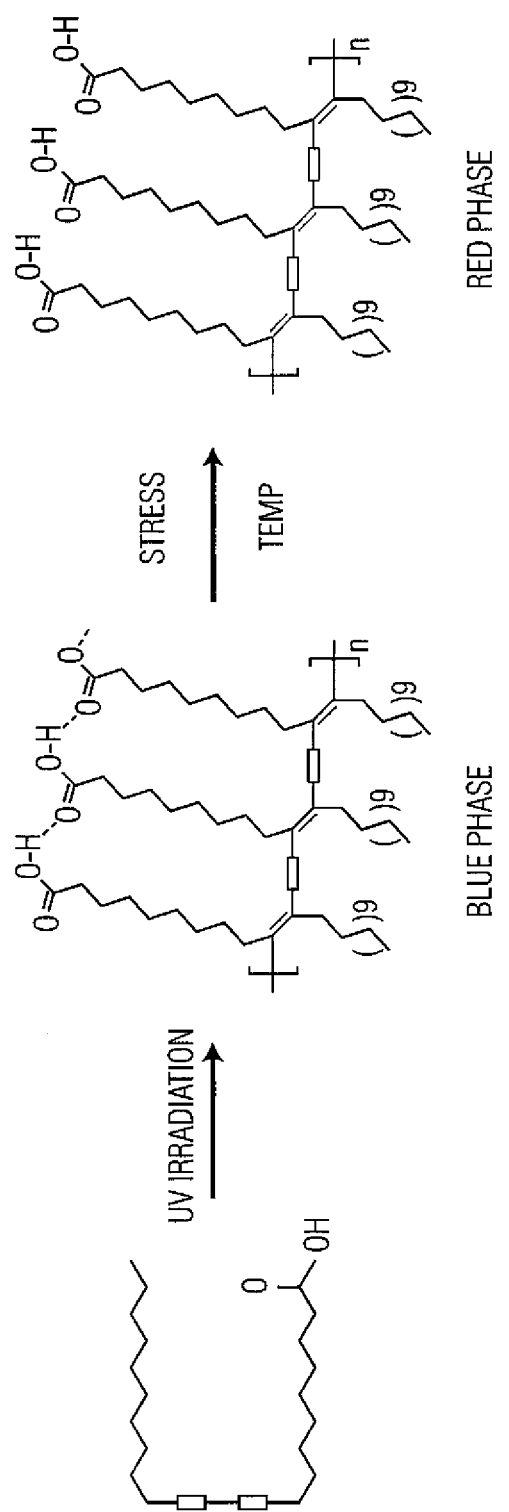
FIG. 1 is flow diagram illustrating the monomer to polymer transition, as well as the blue to red phase transition, of PDAs of the present invention.

As mentioned above, the present invention provides a thermal indicating composition comprising one or more polydiacetylenes; and an oxide comprising ZnO which is alloyed with one or more metal oxides, wherein the ZnO and metal oxide(s) used are in the form of micro scale or smaller particles. Such a composition is preferably incorporated into the form of an ink, paint, spray or other type of coating for application and use. Accordingly, any conventional components required for the production of such coating may be included, such as polymeric binders, plasticizers, UV absorbents, etc.

Preferably, the polydiacetylenes are present in an amount of 1 to 5 weight percent, based on the total weight of the composition. More preferably, the polydiacetylenes are present in an amount of 2.0 to 3.0 weight percent. An important factor in choosing the particular PDA, or combination thereof, is the phase reversibility desired. Chemical methods can be used to control the reversibility of thermochromic materials. In PDAs, the aromatic interactions between the head groups can be modified to control the amount of reversibility of the polymers or even make the polymer irreversible if desired, which is an object of the present invention. Strong head group interactions involving both H-bonding and aromatic bonding lead to reversibility. Accordingly, this issue is addressed by the present invention.

In a preferred embodiment, the composition comprises one or more of $CH_3(CH_2)_{11}$—C≡C—C≡C—$(CH_2)_8$—COOH (10,12 pentacosadiynoic acid, also referred to as "PCDA"), $CH_3(CH_2)_9$—C≡C—C≡C—$(CH_2)_8$—COOH (10,12 tricosadiynoic acid, also referred to as "TCDA"), and HOOC—$(CH_2)_8$—C≡C—C≡C—$(CH_2)_8$—COOH (10,12 docosadiynedioic acid, also referred to as "Bis-1"). PCDA and TCDA were found to show a blue to red transition with brighter contrast in the polymer phase compared with Bis-1. PCDA and TCDA were therefore incorporated in most of the exemplary and test formulations prepared. However, Bis-1 was added to either PCDA or TCDA in the higher temperature formulations to fine-tune the transition temperature. It should be noted that the composition may also comprise unpolymerized diacetylene monomers.

With regards to the oxide alloy component of the composition, the oxide alloy is present in an amount of from 0.01 to 2.0 weight percent, and is defined by the following formula: $Met_{1-x}Zn_xO_y$; wherein, Met is a transition metal, and x is a natural number from 0.2 to 0.6. Preferably, Met is one or more of Zr and Ti. Preferably, the oxide is nanoparticle ZnO having an average particle size of 20-400 nm, more preferably 100-300 nm. Likewise, the $ZrO_2$ and/or $TiO_2$ are microsized particles, preferably nanocrystalline particles, with an average particle size of 100-300 nm.

With regards to the ZnO and oxide alloy containing same, the present inventors found that ZnO uniquely forms a weak complex with acidic diacetylenes containing carboxylic groups, such as 10, 12-pentacosadiynoic acid (PCDA), 10, 12-docosadiynedioic acid (DCDA), and 10, 12-tricosadiynoic acid (TCDA) mentioned above, resulting in reversal of the chromatic blue to red transition. However, it was unexpectedly discovered that this reversibility characteristic is slowed down by mixing the PDA with an alloy of ZnO with $ZrO_2$, i.e., the oxide alloy claimed herein. Accordingly, importantly, it was unexpectedly discovered that combining an oxide alloy with one or more PDAs enables the mixed oxide-PDA compositions of the present invention to function as elapsed time-temperature indicators.

More specifically, it should be noted that pure $ZrO_2$ or $TiO_2$ does not affect the irreversibility of the chromatic transition, but thermally alloying $ZrO_2$ with ZnO was unexpectedly found to substantially slow down the rate of color change, i.e., the conversion of the red to the blue phase. Initial x-ray studies indicated no change in crystal structure of ZnO on thermal treatment with $ZrO_2$. The effect observed may therefore be due to an increase in particle size of ZnO with thermal treatment resulting in a decrease of the interaction of ZnO with the PDA molecule.

Synthesis of the polydiacetylene and alloyed $ZnO/ZrO_2$ compositions of the present invention were carried out on a laboratory scale. A representative process involved the preparation of a PCDA, ZnO and $ZrO_2$ composition of the present invention. Wherein, PCDA was purchased from GFS Chemicals, Powell, Ohio, and nanocrystalline (nc) powders of ZnO and $ZrO_2$ from Sigma-Aldrich St. Louis, Mo. A mixture of nominal composition $Zn_{0.2}Zr_{0.8}O_y$, was finely ground using a mortar and pestle, transferred to a ceramic boat and heated in a furnace in air at 1100° C. for about 7 hrs. The heat-treated $ZnO/ZrO_2$ mixture was then ground into a fine powder and mixed with PCDA monomer to prepare composites of PCDA by suspension in chloroform. The $PCDA-ZnO/ZrO_2$ suspension was sonicated in water bath at room temperature for about 30 min and drops of suspension were deposited on a glass slide followed by solvent evaporation to form thin films, which were polymerized to blue phase Poly $PCDA-ZnO/ZrO_2$ composites by irradiating with a 254 nm wavelength UV source.

In a preferred embodiment, nanosized zinc oxide (ZnO) or a heat treated oxide alloy of ZnO and zirconium oxide ($ZrO_2$) is mixed into the thermal indicating coating composition to control the reversibility of the chromatic transition. In particular, reversing of the red phase to the blue phase can be slowed down by using a mixed oxide of zinc and zirconium, $ZnO/ZrO_2$, preferably thermally alloyed, in compositions near $Zr_{1-x}Zn_xO_y$, where x=0.4. This interaction is believed to lead to the reversibility of the red phase, and sizeable increase of the chromatic transition temperature in the poly-PCDA-ZnO nanocomposites.

Figure 2:
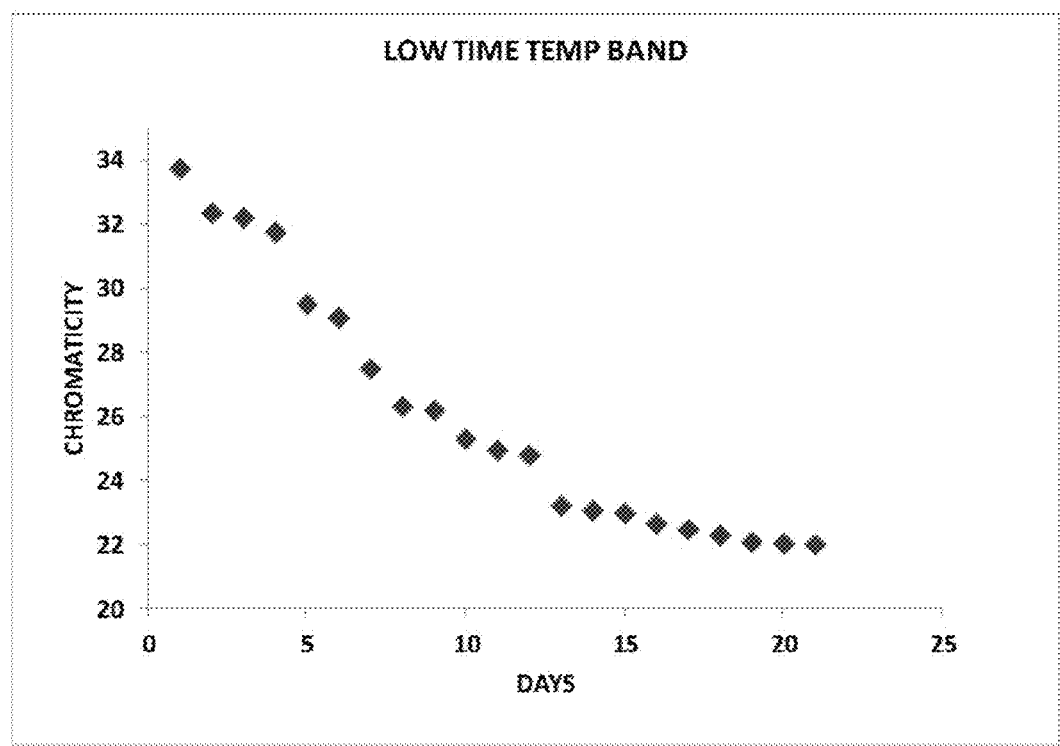
FIG. 2 is a graph of the Chromaticity over exposure time to a low temperature band, 145° F. to 164° F. of a formulation of the present invention.
Figure 3:
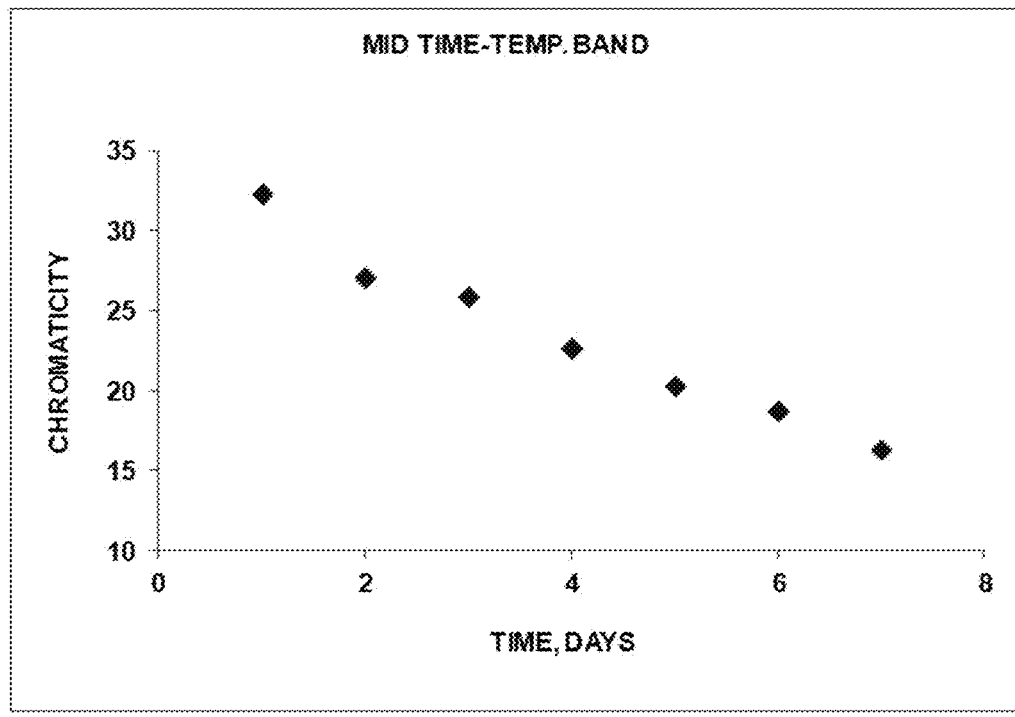
FIG. 3 is a graph of the Chromaticity over exposure time to a mid-temperature band, 165° F. to 184° F. of a formulation of the present invention.

To prove the cumulative time indication ability of formulations of the present invention—a PDA was combined with an alloyed zinc and zirconium composition of the formula $Zr_{1-x}Zn_xO_y$, where x=0.4, i.e. $Zr_{0.6}Zn_{0.4}O_y$, which combination was mixed with a PMMA, a polymer, and a commercial white paint—to form low (145° F. to 164° F.) and mid-temperature (165° F. to 184° F.) cumulative time indicating formulations. The inventive composition used in the low range was 40.39% by weight exterior base commercial paint, 2.83% diacetylene (10, 12 tricosadiynoic acid), 28.27% PMMA, 10.11% PACBCS, 14.13% PVA, 4.40% Cerium Oxide, and 0.08% mixture of oxides (ZnO and $ZrO_2$), 0.08% HAL (hindered amine light stabilizer) and diluted with acetone (or similar solvent) to 100 ml of paint. The inventive composition used in the mid-temperature range was 40.39% by weight exterior base commercial paint, 2.83% diacetylene (10, 12 pentacosadiynoic acid), 28.27% PMMA, 10.11% PACBCS, 14.13% PVA 4.40% Cerium Oxide and 0.08% mixture of oxides (ZnO and $ZrO_2$), 0.08% HAL and diluted with acetone (or similar solvent) to 100 ml of paint. The chromaticity values measured by an X-Rite Model 518 Optical Densitometer, X-Rite Corporation, Grand Rapids, Mich., versus cumulative time in the low- and mid-temperature ranges are shown in FIGS. 2 and 3. The chromaticity values obtained being proportional to how close the color is to either a gray or pure hue of the original color.

Figure 4:
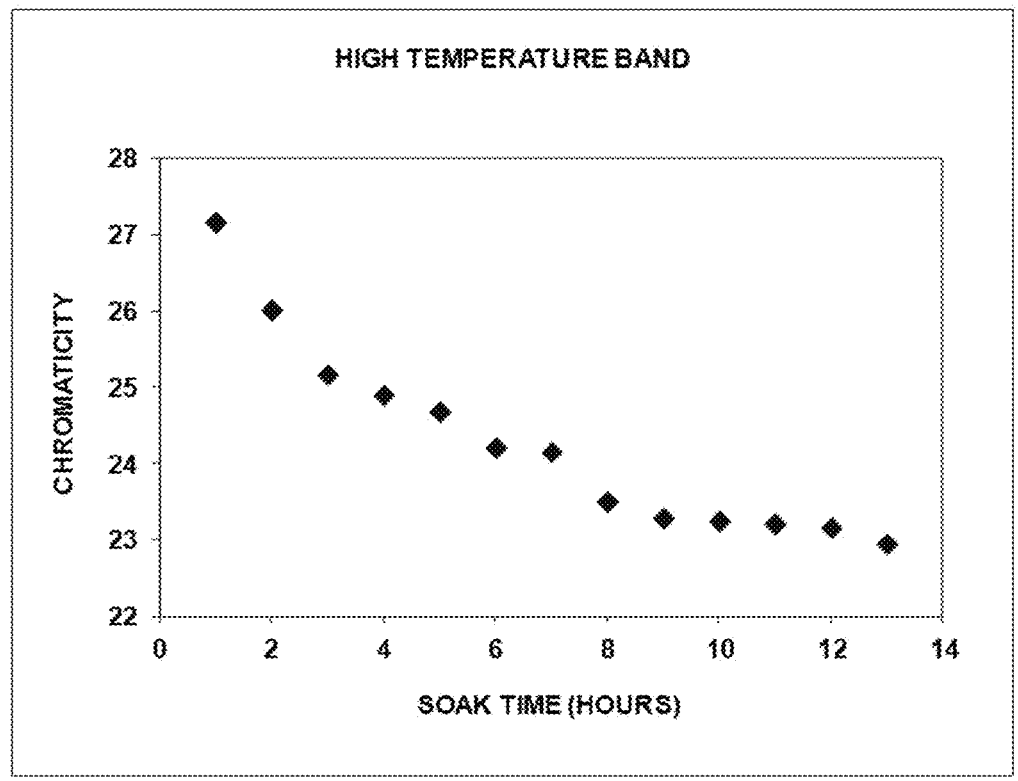
FIG. 4 is a graph of the Chromaticity over exposure time to a high-temperature band, above 185° F. of a formulation of the present invention.

In contrast, a high-temperature range (above 185° F.) indicator was formed using a higher concentration of ZnO in the alloy with the $ZrO_2$, because a shorter soak time at the elevated temperature is required. The composition comprising 40.39% by weight of exterior base commercial paint, 2.83% mixture of diacetylenes (10, 12 nanocosadiynoic acid and 10, 12 docosadiynoic acid), 28.27% PMMA, 10.11% PACBCS, 14.13% PVA, 4.40% Cerium Oxide, 0.08% mixture of oxides (ZnO and $ZrO_2$), and 0.08% HAL and diluted with acetone (or similar solvent) to 100 ml of paint. The chromaticity values at the high-temperature range are shown in FIG. 4.

As mentioned above, in addition to the two inventive components, any additional paint/coating/spray additives may be included in the composition, as long as they do not interfere with the thermal indicating characteristics of the composition. In a preferred embodiment, the thermal indicating composition comprise one or more of polyurethane, polyvinyl alcohol (PVA), polyvinyl pyrollidone (PVP), polyvinylidene fluoride (PVDF), and polymethylmethacrylate (PMMA), cellulose, aluminum oxide, titanium oxide, fuming silica, barium sulfate, and cyclodextrin. PVA (polyvinyl alcohol), PVP (polyvinyl pyrollidone) or polyvinylidene fluoride (PVDF) to control the temperature of the chromatic blue to red transition via hydrogen bonding interactions. PMMA (polymethylmethacrylate) was added for uv-protection of the formulation. A sprayable blend was fabricated by formulating the thermochromic PDA precursor mixed with PVA, PVP or PVDF with a commercial white paint.

The transition temperature ranges of the thermal indicating compositions are mainly controlled by the types of polydiacetylenes (PDAs) included in the thermal indicating composition, which change in each temperature band (range). Further, varying the proportions of the oxide alloy within the composition affects all the three factors, i.e., irreversibility, reversibility and indicating range. And, each type of polydiacetylene interacts differently with the oxide alloy. Moreover, the amount of alloy with respect to PDA significant affects the characteristics of the thermal indicating composition.

In summary, it is believed that the type of polydiacetylene is what sets the initial temperature trigger ranges. Adding ZnO thereto causes reversibility by repairing the hydrogen bonds; but, by itself ZnO functions merely to enable reversible color change, as well as an upshift in temperature trigger range when added in certain concentrations. However, it was unexpectedly discovered that the addition of an oxide comprised of ZnO, form of micro scale or smaller particles, alloyed with a transition metal oxide, such as $ZrO_2$ and or $TiO_2$, form of micro scale or smaller particles, slows the ZnO induced reversibility and provides control over the soak times.

PREPARATION EXAMPLES

Example #1

Thermal Indicating Composition Operable to Indicate Exposure to a Temperature Range of from 95° C.-100° C.

A composition was prepared by mixing the following components in the following weight percents:
40.39 wt % exterior base commercial paint (liquid paint);
2.83 wt % of a mixture of 10, 12 tricosadiynoic acid, and 10, 12 docosadiynoic acid;
28.27 wt % PMMA (polymethylmethacrylate);
10.11 wt % PACBCS (polyacrylonitrile-co-butadiene-co-styrene);
14.13 wt % PVA (poly vinyl acetate);
4.40 wt % cerium oxide used as a uv-blocker;
0.08 wt % of an oxide alloy of ZnO and $ZrO_2$; and
0.08 wt % HAL (hindered amine light stabilizer) and diluted to 100 ml of paint, used to stabilize the color of the paint.

Note: Two classes of hindered amine light stabilizers, HALS, can be used to stabilize the color of the paints, including: (i) poly[[6-[(1,1,3,3-tetramethylbutyl)amino]-s-triazine- 2,4-diyl]-[(2,2,6,6-tetramethyl-4-piperidyl)imino]-hexamethylene-[(2,2,6,6-tetramethyl-4-piperidyl)imino], (HAL-1) and (ii) Bis(2,2,6,6-tetramethyl-4-piperidyl)sebacate (HAL-2). Anti-oxidant (AO) also used for stabilization was: 1,5,8,12-Tetrakis[4,6-bis(N-butyl-N-1,2,2,6,6-pentamethyl-4-iperidylamino)-1,3,5-triazin-2-yl]-1,5,8,12-tetraazadodecane. And, U-V protection and maintenance of the gloss of the paint were achieved by inclusion of PMMA, PVA and PACBCS in the inventive paint formulation.

Example 2

Thermal Indicating Composition Operable to Indicate Exposure to a Temperature Range of from 80° C.-85° C.

A composition was prepared by mixing the following components in the following weight percents:
40.39 wt % exterior base commercial paint (liquid);
2.83 wt % of a mixture of 10, 12 nanocosadiynoic acid, and 10, 12 docosadiynoic acid;
28.27 wt % PMMA;
10.11 wt % PACBCS;
14.13 wt % PVA;
4.40 wt % cerium oxide;
0.08 wt % of an oxide alloy of ZnO and $ZrO_2$; and
0.08% HAL (hindered amine light stabilizer) and diluted to 100 ml of paint.

Example 3

Thermal Indicating Composition Operable to Indicate Exposure to a Temperature Range of from 65° C.-70° C.

A composition was prepared by mixing the following components in the following weight percents:
40.39 wt % exterior base commercial paint (liquid);
2.83 wt % of 10, 12 pentacosadiynoic acid;
28.27 wt % of PMMA;
10.11 wt % of PACBCS;
14.13 wt % of PVA;
4.40 wt % of cerium oxide;
0.08 wt % of an oxide alloy of ZnO and $ZrO_2$; and
0.08% HAL (hindered amine light stabilizer) and diluted to 100 ml of paint.

Example 4

Thermal Indicating Composition Operable to Indicate Exposure to a Temperature Range of from 55° C.-60° C.

A composition was prepared by mixing the following components in the following weight percents:
40.39 wt % of exterior base commercial paint (liquid);
2.83 wt % of 10, 12 tricosadiynoic acid;
28.27 wt % PMMA;
10.11 wt % PACBCS;
14.13 wt % PVA;
4.40 wt % cerium oxide;
0.08 wt % of an oxide alloy of ZnO and $ZrO_2$; and
0.08% HAL (hindered amine light stabilizer) diluted to 100 ml of paint.

Generally, preparation of a thermal indicating paint of the present invention as a coating/paint, was conducted in the following steps: (1) an exterior paint is first diluted with methylene chloride via conventional methods, such as ultra sonication, for about 5 minutes; (2) then, the paint is further diluted by adding acetone thereto and mixing the paint and acetone; (3) the polymers PMMA, PVA and PACBCS are mixed into the diluted paint obtained above, and then the paint is further thinned down by adding additional acetone; and (5) finally the polydiacetylenes, the oxide alloy (such as ZnO/$ZrO_2$, as described above), HALS and cerium oxide are added to the diluted and thinned paint, and mixed therein using a magnetic stirrer for about two days or more to obtain satisfactory homogeneity and viscosity, thereby forming a thermal indicating coating composition.

To form a thermal indicating test strip/test plate, about 10 ml of the thermal indicating coating composition, as described above, is spread on metal panels by using a paint sprayer. The solvent is then allowed to evaporate at room temperature. The resulting dried paint/coating on the metal panels is then UV irradiated for a few minutes to cause the paint to enter the blue phase.

What is claimed is:

1. A thermal indicating composition comprising:
   (a) one or more polydiacetylenes; and
   (b) ZnO alloyed with one or more, transition metal oxides to form an allow oxide,
   (c) wherein, the ZnO and transition metal oxides used are micro scale or smaller particles.

2. The thermal indicating composition of claim 1, wherein the composition comprises:
   (a) 1 to 5 weight percent of the one or more polydiacetylenes; and
   (b) 0.01 to 2.0 weight percent of the oxide alloy.

3. The thermal indicating composition of claim 1, wherein the composition comprises:
   (a) 2.0 to 3.0 weight percent of the one or more polydiacetylenes; and
   (b) 0.01 to 2.0 weight percent of the oxide alloy.

4. The thermal indicating composition of claim 1, wherein the oxide alloy is defined by the following formula: $Met_{1-x}Zn_xO_y$; wherein, Met is a transitional metal, and x is a natural number from 0.2 to 0.6.

5. The thermal indicating composition of claim 4, wherein the oxide alloy is comprised of ZnO/$ZrO_2$ or ZnO/$TiO_2$, or a combination thereof.

6. The thermal indicating composition of claim 1, wherein the polydiacetylenes are selected from 10,12 pentacosadiynoic acid (PCDA), 10,12 tricosadiynoic acid (TCDA), and 10,12-docosadiynedioic acid (Bis-1), 10, 12 nanocosadiynoic acid, and 10, 12 docosadiynoic acid or a combination thereof.

7. The thermal indicating composition of claim 1, further comprising one or more of polyurethane, polyvinyl alcohol (PVA), polyvinyl pyrollidone (PVP), polyvinylidene fluoride (PVDF), and polymethylmethacrylate (PMMA), cellulose, aluminum oxide, titanium oxide, fuming silica, barium sulfate, and cyclodextrin.

8. The thermal indicating composition of claim 1, wherein the ZnO of the oxide alloy is nanoparticle ZnO having an average particle size of 20-400 nm.

9. The thermal indicating composition of claim 1, wherein the ZnO of the oxide alloy is nanoparticle ZnO having an average particle size of 100-300 nm.

10. The thermal indicating composition of claim 1, wherein the transition metal of the oxide alloy is nanocrystalline $ZrO_2$ and/or nanocrystalline $TiO_2$ having an average particle size of 100-300 nm.

* * * * *